(12) United States Patent
Nash et al.

(10) Patent No.: US 7,560,109 B2
(45) Date of Patent: Jul. 14, 2009

(54) IMMUNOGEN ADHERENCE INHIBITOR DIRECTED TO LACTIC ACID PRODUCING ORGANISMS AND METHOD OF MAKING AND USING IT

(75) Inventors: Peter Nash, Eden Prairie, MN (US); Bradley M. Mitteness, Ghent, MN (US)

(73) Assignee: Camas Incorporated, Le Center, MN (US)

( * ) Notice: Subject to any disclaimer, the term of this patent is extended or adjusted under 35 U.S.C. 154(b) by 0 days.

(21) Appl. No.: 11/786,525

(22) Filed: Jul. 12, 2007

(65) Prior Publication Data

US 2007/0253947 A1 Nov. 1, 2007

Related U.S. Application Data

(60) Division of application No. 10/658,491, filed on Sep. 8, 2003, now Pat. No. 7,238,351, which is a continuation-in-part of application No. 10/038,260, filed on Jan. 7, 2002, now Pat. No. 7,256,270, which is a division of application No. 09/616,843, filed on Jul. 14, 2000, now Pat. No. 7,241,443.

(60) Provisional application No. 60/201,268, filed on May 2, 2000, provisional application No. 60/143,985, filed on Jul. 15, 1999.

(51) Int. Cl.
*A61K 39/395* (2006.01)
*A61K 39/40* (2006.01)
*A61K 35/66* (2006.01)
*C07K 16/02* (2006.01)

(52) U.S. Cl. ............... 424/130.1; 424/164.1; 435/253.6; 435/340; 530/389.5

(58) Field of Classification Search ........................ None
See application file for complete search history.

(56) References Cited

U.S. PATENT DOCUMENTS

| | | |
|---|---|---|
| 3,794,732 A | 2/1974 | Raun |
| 3,878,298 A | 4/1975 | Parish et al. |
| 3,917,818 A | 11/1975 | Botes |
| 3,937,836 A | 2/1976 | Raun |
| 4,166,867 A | 9/1979 | Betz et al. |
| 4,550,019 A | 10/1985 | Polson |
| 4,748,018 A | 5/1988 | Stolle et al. |
| 4,933,364 A | 6/1990 | Ivy et al. |
| 5,080,895 A | 1/1992 | Tokoro |
| 5,196,193 A | 3/1993 | Carroll |
| 5,367,054 A | 11/1994 | Lee |
| 5,443,976 A | 8/1995 | Carroll |
| 5,585,098 A | 12/1996 | Coleman |
| 5,725,873 A | 3/1998 | Cook et al. |
| 5,741,489 A | 4/1998 | Pimentel |
| 5,753,228 A | 5/1998 | Sterling et al. |
| 5,753,268 A | 5/1998 | Stolle et al. |
| 5,919,451 A | 7/1999 | Cook et al. |
| 5,965,128 A | 10/1999 | Doyle et al. |
| 6,083,500 A | 7/2000 | Wooley et al. |
| 6,086,878 A | 7/2000 | Adalsteinsson et al. |
| 6,217,865 B1 | 4/2001 | Hunchar |
| 6,287,555 B1 | 9/2001 | Gill et al. |
| 6,419,926 B2 | 7/2002 | Kodama et al. |
| 6,632,439 B2 * | 10/2003 | Liem et al. ................ 424/234.1 |
| 2002/0106397 A1 * | 8/2002 | Nash et al. .................. 424/439 |

OTHER PUBLICATIONS

Abaza et al., J of Protein Chemistry 11(5): 433-444, 1992.
Adesiyun et al, Br Vet J 48(6): 547-56, 1992.
Charley, Helen and Weaver, Connie; "Foods: a Scientific Approach;" Third Edition; Merrill/Prentice Hall; New Jersey 1998; p. 350.
Chen et al, More Monensin-Sensitive, Ammonia Producing Bacteria from the Rumen, Applied and Environmental Microbiology, May 1989, pp. 1052-1057.
Cooper et al.; "Effect of Rumesin and Feed Intake Variation on Ruminal pH;" 1997 Beef Index Report; http://animalscience.unl.edu/beef/br97/EFFRUMEN.html; pp. 49-52.
Damron, W. Stephen; "Introduction to Animal Science: Global, Biological, Social and Industry Perspectives;" Prentice Hall; New Jersey 2000; pp. 57-58.
Drause et al., An rRNA Approach for assessing the role of olibgate amino acid-fermenting bacteria in ruminal amino acid deamination, Mar. 1996, Appl Environ Microbiol 62(3): 815-821.
Gansheroof et al., *Escherichia coli* 0157:H7 in beef cattle presented for slaughter in U.S., Proc. Natl. Acad. Sci., Mar. 28, 2000, pp. 2959-2961.
Goad et al.; "Ruminal Microbial and Fermentative Changes Associated with Experimentally Induced Subacute Acidosis in Steers;" J. Anim. Sci., Vo. 76, US 1998; pp. 234-241.
Godfrey, et al.; "Virginiamycin to Protect Sheep Fed Wheat, Barley or Oats from Grain Poisoning under Simulated Drought Feeding Conditions;" Aust. J. Agric. Res, vol. 46; Australia 1995; pp. 393-401.
Herzberg et al, Degree of Immunity Induced by Killed Vaccines to Experimental Salmonellosis in Mice, Infection and Immunity, Jan. 1972, pp. 83-90.
Kaspers et al, Zentralbl Veterinarmed A 43(4): 225-31, Jun. 1996.
Krause et al., An rRNA Approach for Assessing the Role of Obligate Amino Acid-Fermenting Bacteria in Ruminal Amino Acid Deamination, Applied and Enviromental Microbiology, Mar. 1996, pp. 815-821.
Kuby et al, Immunology, Second edition, pp. 86-96, 1994.
Lana et al., Influence of Monensin on Holstein Steers Fed High-Concentrated Diets Containing Soybean Meal or Urea, Journal Anim. Sci. 1997, pp. 75:2571-2579.

(Continued)

*Primary Examiner*—Phuong Huynh
(74) *Attorney, Agent, or Firm*—Z. Peter Sawicki; Westman, Champlin & Kelly, P.A.

(57) ABSTRACT

A microbial adherence inhibitor in the form of fowl egg antibodies is disclosed, along with the method of making it and methods of using it. The inhibitor functions by substantially preventing the attachment or adherence of colony-forming immunogens in the rumen and intestinal tracts of host food animals. The use of antibodies against *Fusobacterium necrophorum* adherence antigens decreases the colonization of *F. necrophorum* sufficiently to reduce or eliminate the incidence of liver abscesses in the animals.

5 Claims, 1 Drawing Sheet

OTHER PUBLICATIONS

Nagaraja, T.G. and Chegappa; M.M.; "Liver Abscesses in Feedlot Cattle: A Review;" J. Anim. Sci., vol. 76; US 1998; pp. 287-298.

Nocek, James E.; "The Link Between Nutrition, Acidosis, Laminitis and Environment;" http://www.afns.ualberta.ca/Hosted/WCDS/Proceedings/1996/wcd96049.htm; Canada 1996; pp. 1-13.

Owens et al.; "Acidosis in Cattle: A Review;" Journal of Animal Science, vol. 76, Issue 1; US 1998; pp. 275-286.

Pate, F., Ionophores Do Not Appear to Work in Molasses Supplements, The Florida Cattleman and Livestock Journal, Nov. 1996.

Pell et al., J Dairy Sci 80: 2673-2681, 1997.

Plaizier et al.; "Studies on the Rumen Physiology and Metabolic Function with Pre- and Postpartum Administration of Rumensin CRC in the Dairy Cow;" http://home.cc.umanitoba.caj-plazier/monensin.html; Canada; pp. 1-11.

Russel, James B. and Hino, Tsuneo; "Regulation of Lactate Production in *Streptococcus bovis*: A Spiraling Effect that Contributes to Rumen Acidosis;" Journal of Dairy Science, vol. 68; US 1985; pp. 1712-1721.

Russell, J.B., Rumen Bacteria Rob Cattle of Nutrients, Agricultural Research, May 1993, pp. A43-44.

Stryer et al, in Biochemistry, Third edition, W.H. Freeman Company, New York, pp. 31-33, 1998.

Sugita-Konishi et al., Biosci Biotechnol Biochem 60(5): 886-8, May 1996.

Trinchieri et al, Urol Res 18(5): 305-8, 1990; abstract.

Yokoyama et al., Vaccine 16(4): 388-93, Feb. 1998.

Yokoyama et al, Infection and Immunity 60(3): 998-1007, Mar. 1992.

* cited by examiner

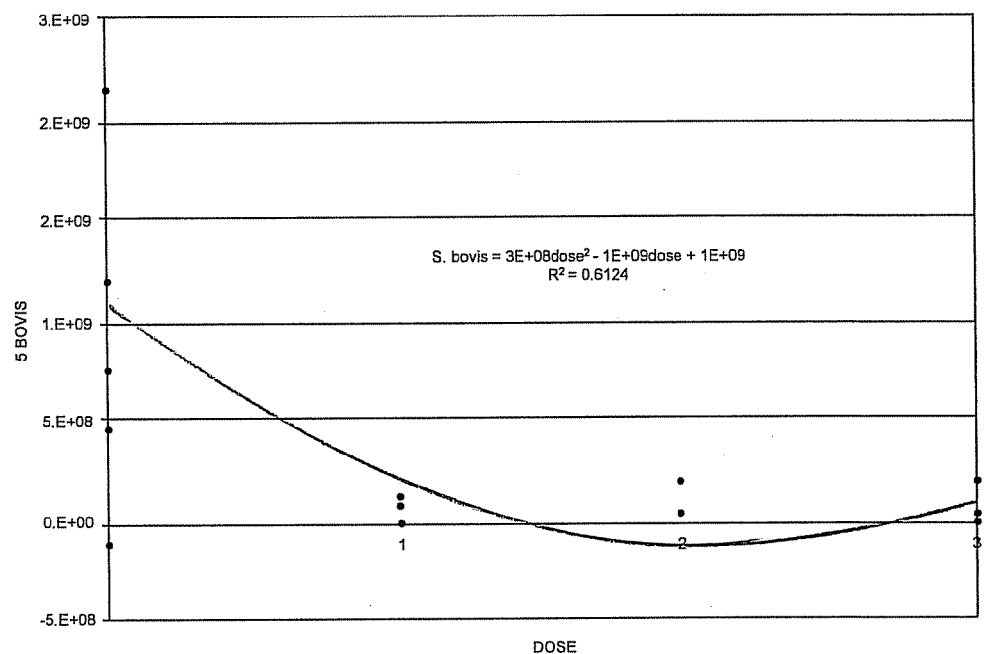
Figure 1. Response by S. bovis collected in rumen fluid of cattle exposed to increasing doses of a polyclonal antibody specific against S. bovis fed for 14 days.

IMMUNOGEN ADHERENCE INHIBITOR DIRECTED TO LACTIC ACID PRODUCING ORGANISMS AND METHOD OF MAKING AND USING IT

CROSS REFERENCE TO RELATED APPLICATIONS

This application is a divisional of U.S. application Ser. No. 10/658,491, filed on Sep. 8, 2003, which is a continuation-in-part of U.S. application Ser. No. 10/038,260 filed on Jan. 7, 2002, which is a divisional application of Ser. No. 09/616,843, filed Jul. 14, 2000 which is a non-provisional application related to provisional application Ser. No. 60/201,268 filed on May 2, 2000 and provisional application Ser. No. 60/143,985, filed on Jul. 15, 1999.

FIELD OF THE INVENTION

This invention is directed to microbial adherence inhibitors in the form of fowl egg antibodies for substantially preventing the attachment or adherence of colony-forming immunogens or haptens in the rumen and intestinal tract of host food animals, to the method of producing each adherence inhibitors, and to the methods of using such inhibitors to: (1) promote the growth of food animals by improving feed conversion rates be decreasing the lactic acid production organisms in food animals, and (2) to substantially reduce or eliminate the microorganisms that reduce pH and cause problems in the liver and rumen, and erratic fee intake and (3) to reduce the incidence of microorganisms that can escape the rumen and cause liver abscesses and laminitis.

BACKGROUND OF THE INVENTION

Certain common bacterial immunogens in the rumen can produce large amounts of lactic acid. These include but are not limited to *Streptococcus bovis* and *Lactobacillus* spp. As the host consumes starch in the diet, these deleterious organisms produce very high amounts of lactic acid that can result in reduced performance and, in acute situations, dangerously low pH rumen levels. Once the pH lowers in the rumen, these bacterial species become the primary etiologic agents in rumen abscesses.

Lactic acid acidosis is produced in ruminants fed diets high in grain. These grain-fed animals are subject to a number of nutritional or metabolic problems, but most are secondary to acute acidosis. Lactic acidosis occurs when there is an abrupt increase in the intake of readily fermentable carbohydrates. A typical example would occur when range or pasture fed cattle, which may never have been fed grain in their lives, are brought into a feedlot and fed grain. If the amount of grain fed exceeds the ability of the rumen microbial population to move in an orderly transition from primary cellulite based to a starch-based diet, there is a shortage of amylolytic organisms. The void is quickly occupied by a fast growing amylolytic bacteria, *Streptococcus bovis*, which grows rapidly and produces lactic acid as a fermentation end product, particularly D-lactate which is poorly absorbed and metabolized. *Lactobacillus* spp. also produces lactate. As *S. bovis* increases, the rumen pH drops, causing spiraling accumulation of lactic acid in the rumen and a consequent lower pH. The accumulation of lactic acid in the rumen and blood causes rumen acidosis and metabolic acidosis. This has a corrosive affect on the rumen wall and causes the papillae to peel off. Absorption is impaired and bacteria inside the rumen wall can gain system entrance. A high incidence of liver abscesses can result. Additionally, lower rumen pH can inhibit the growth of all organisms, including beneficial microbes that aid in efficient feed digestion.

Chronic liver abscesses reduce growth rates, feed efficiency, and carcass dressing percentage. The incidence of liver abscess in feedlot cattle is 12-32%. It is a major economic import because of carcass condemnation and reduced animal performance. These ruminal lesions foster an invasion of bacterium, principally *Fusobacterium necrophorum*. It is generally accepted that the rumen lesions resulting from acidosis are the predisposing factors for liver abscesses. *F. necrophorum* prosseses a number of virulent factors that allow the organism to enter and colonize the rumen epithelium and subsequently enter and establish an infection in the liver.

The accumulation of lactic acid in the rumen increases the osmolotity of the rumen, drawings water from the blood into the rumen and causing dehydration. Recovery at this stage is unlikely. Absorbed acid may cause systematic acidosis with a lowered blood pH, electrolyte imbalance, and lead to kidney failure.

Acute lactic acidosis causes dramatic increases in rumen acidity and osmololity causing sever rumenity. Decrease blood pH, fatal dehydration, and chronic acidosis reduce feed intake and animal performance in feedlot cattle and diary cattle.

Acidosis is not readily treated but best prevented. Antibiotics can be used to contain *S. bovis* and *Lactobacillus* spp.

Normally the rumen environment is anaerobic with pH of approximately 6.5. Rumen pH levels between 5.2 and 5.6 define sub-acute acidosis. Acute acidosis is when the rumen pH level dips below 5.2. the use of monensin, a feed additive marketed under the name Rumensin, has potential to improve health and production of dairy on high concentrate diets but not fully prevent ruminal acidosis. In many diary operations, the challenge is not with acute but sub-clinical acidosis. Monensin, however, is not cleared for use in lactating dairy cows.

The cascade effects of acidosis originating from the initial ingestion of carbohydrate depend upon the intensity and duration of the insult. The most critical is the pH threshold. This related to microbial growth rates and shifts in rumincal population, and significantly influences the systemic metabolic state.

A principal objective of the present invention is to substantially prevent the colonization of deleterious organisms such as *S. bovis*, *Lactobacillus* spp. and *F. necrophorum*, as well as the growth of such organisms in the rumen and the intestinal tracts of food animals resulting in their substantial elimination from the animal by the administration of fowl egg antibody to the specific organisms.

Haptens are partial or incomplete immunogens such as certain toxins, which cannot by themselves cause antibody formation but are capable of combining with specific antibodies. Such haptens may include bacterial toxin, yeast mold toxin, viruses, parasite toxins, algae toxins, etc.

Under the most popular current feeding system, food animal fee efficiency is enhanced through the use of ionophores such as monensin, feed additive marketed under the trade name Rumensin. this is a class of polyester antibiotics approved for feed given to beef cattle and diary heifers, but is not approved for use with lactating diary cattle. Most gram-positive microorganisms are non-specifically, vulnerable to the ionophores, antibiotics that can be quite toxic to the host animal if used improperly. As these antibiotics are not specific, many of the ruminal microorganisms required to digest the cellulose of ingested plant material may also be affect. The problem with carry over and development of resistant strains of microorganisms are also of major concern to the industry. The use of broad-spectrum antibiotics has further drawbacks including vulnerability to human error, additional cost, consumer resistance, and the like. In addition, the monensin type additive cannot be added with the commonly used molasses-based supplements.

PRIOR ART

The production of avian egg antibody for the diagnosis or treatment of specific conditions has been known. The production of avian egg antibody for the inhibition of organisms, specifically the colonization of non-illness causing acidosis organisms, and the adherence and colonization of illness-causing immunogens is not suggested.

Representative prior art patents including the following:
Polson, U.S. Pat. No. 4,550,019
Stolle et al., U.S. Pat. No. 4,748,018
Tokoro, U.S. Pat. No. 5,080,895
Carroll, U.S. Pat. No. 5,196,193
Lee, U.S. Pat. No. 5,367,054
Coleman, U.S. Pat. No. 5,585,098
Stolle et al., U.S. Pat. No. 5,753,268
Cook and Jerome, U.S. Pat. No. 5,919,451

Raun, U.S. Pat. No. 3,794,732, discusses the uses of polyester antibiotics in ruminant rations to improve the utilization of feed in ruminant animals. This specifically addresses the use of antibiotics in ruminant animals as growth promotants.

Raun, U.S. Pat. No. 3,947,836, discusses the use of specific antibiotic compounds for ruminant feed utilization improvement when given orally to the animal. Specifically, the animal develops rumen function where more propionates in relation to acetates are produced thus improving feed utilization.

Ivy et al., U.S. Pat. No. 4,933,364, discusses an alternative process for promoting growth and feed efficiency of food producing animal. They propose the use of zinc antibiotic that can be added in insoluble form to create a zinc antibiotic complex, which enhances feed efficiency of food producing mammals. They reference two U.S. Pat. Nos. 3,501,568 and 3,794,732 that cover monensin in great detail.

Other references on the use of additives such as monensin have mentioned the need for wise application of this material because thy can be toxic to some animals, such as horses. These antibiotics, which are not approved for use in dairy cows, must be administered carefully. In addition, feed intake is initially reduced, as monensin cannot be added to molasses based supplements, which are classic additives to cattle feeds.

Polson, U.S. Pat. No. 4,550,019, is directed to the manufacture and use of fowl egg yolk antibodies for making immunological preparations for the passive immunizations of animals, including humans, as immuno reagents for immunosorbitive processes and in particular for quantitative analytical tests, especially micro assays for diagnostic, pathological, forensics, and pharmacokinetic investigations.

Stolle et al., U.S. Pat. No. 4,748,018, is directed to a method of passive immunization of mammals using avian egg yolk antibody against any of a variety of antigens using various methods of administration under various conditions and using various compositions incorporating the antibody, after first developing in the mammal a tolerance for the antibody.

Tokoro, U.S. Pat. No. 5,080,895 is directed to a specific antibody containing substance from eggs and a method of production and use thereof for the treatment of infectious or other diseases, as additives in food for livestock and poultry, cosmetics, and medicines, and in the field of serodiagnosis. Although not explicitly stated, it is apparent that the use of the egg antibody in feeds is to provide an essay means of oral administration of the antibody for the treatment of intestinal infections in livestock or poultry.

Carroll, U.S. Pat. No. 5,196,193, and a divisional U.S. Pat. No. 5,443,976, are directed to anti-venom compositions containing horse antibody or avian egg yolk antibody for neutralizing snake, spider, scorpion, or jellyfish venom.

Lee, U.S. Pat. No. 5,367,054 is directed to methods for large-scale purification of egg immunoglobulin for the treatment of infections.

Coleman, U.S. Pat. No. 5,585,098 is directed to a method of oral administration of chicken yolk immunoglobulins to lower somatic cell count in the milk of lactating ruminants.

Stolle et al., U.S. Pat. No. 5,753,268, is directed to an anti-cholesterolemic egg vaccine and method for production and use as a dietary supplement for the treatment of vascular disorders in humans and other animals.

Cook et al. U.S. Pat. No. 5,919,451 is directed to a method of improving efficiency of animals between days 29 to 39 days of age to convert feed using a feed particle with an inner core of nutrients and an outer layer with a conjugated fatty acid or antibody specific to endogenous gut peptide.

SUMMARY OF THE INVENTION

Broadly stated, this invention is directed to a method for the production of a microbial adherence inhibitor for administration to host food animals to substantially prevent the adherence of colony-forming immunogens or haptens in the rumen and/or intestinal tract of food animals, which are not by themselves subject to target illness, by first inoculating female birds, in or about to reach their egg laying age, with the particular target immunogen. Then, after a period of time sufficient to permit the production in bird of antibody to the targeted immunogen, the eggs laid by the birds are harvested. The total antibody-containing contents of the eggs are separated from the shells and can be used as a liquid or at least partially dried. The egg content may be dried on a feed extender or carrier material or mixed with liquid extenders such as PBS or liquid molasses. The dried carrier or liquid separated egg adherence inhibiting material may be stored or shipped for use when needed.

The target immunogen with which the bird is inoculated depends upon the anticipated use of the inhibitor, a non-disease-causing lactic acid producing organism where boosting of feed efficiency is the objective, and a targeted disease-causing organism where the objective is the substantial reduction or elimination of illnesses.

The egg contents incorporating the antibody specific to the targeted immunogen are administered to the food animals by distributing the antibody material substantially uniformly throughout an animal feed and then supplying the resulting antibody-containing animal feed to the food animals. When improved feed utilization is the objective, the antibody-containing animal feed is supplied to food animals during the normal finishing schedule prior to slaughter. The substantial prevention of colonization of the targeted organism in the rumen or intestinal tract of the animal will ultimately permit substantial reduction or elimination of the organism form the animal. This repression of colonization and elimination of the subject organism will permit a significant increase in feed efficiency by food production animals. In addition, the resulting decrease in competition by the lactic acid producing organism will further enhance the most efficient utilization of food by the host.

The invention is directed particularly to the production of an adherence inhibitor specific to *S. bovis* and *F. necrophorum* and to the substantial reduction or elimination of gastric problems caused by these bacteria. The invention is described with particular reference to elimination of lactic acid caused by *S. bovis*, and liver abscesses caused by *F. necrophorum*, but it understood that the invention is not limited, but is equally applicable to elimination of illnesses or the elimination of reduced feed efficiencies caused by the other colony-forming immunogens and haptens.

FIG. 1 is a graphical view.

DESCRIPTION OF THE PREFERRED EMBODIMENTS

The present invention is based on the concept of specifically inhibiting the ability of colony-forming lactic acid producing organisms such as *S. bovis* and *F. necrophorum* to adhere in the rumen and intestinal tracts of food animals and thus reduce the ability of the organisms to multiply, grow, and colonize in the animals. Dietary modifications can be designed to make the rumen and intestinal tract less receptive to the organisms over the lifetime of the animal. While the microbial inhibitors of the present invention may be administered at will by the producer, it is preferred for efficient animals feed utilization that a carefully determined and managed course of administration during the finishing period at the feedlot level be scheduled and followed. Such a predetermined period which takes advantage of the low dose, longer cumulative effect, and which is also easily integrated into the current production practices will provide the most economically attractive rate of return through improved animal performance.

For the elimination of lactic acid forming organisms, the inhibitor may be administered either immediately pre-slaughter or over some substantial period of the lifetime of the animal. It is preferred that a carefully determined and managed mid-term period course of administration of the feedlot level be followed.

Any organism that colonizes the rumen or alimentary tract of its host must possess the capability of sticking or adhering to the surface in order to multiply and grow. The specific organism addressed by this invention are no exceptions to this rule. As other facts such as need of beneficial organism for specific enzymes must also be considered, specific reagents are required to reduce the number of targeted organism in the rumen or intestinal tract while not interfering with normal flora. The organism inhibitor of this invention strongly interferes with adherence in a highly specific manner and, on a cumulative basis, thereby prevents the targeted organisms for multiplying, growing, and colonizing. Through the vehicle of a simple daily feed supplement, the product essentially supplies the host with an antibody presentation designed not to cure any disease in the animal, but to dislodge any resident bacteria in the rumen or alimentary tract and to prevent attachment of any newly introduced numbers of that same bacteria. The microbial inhibitor has no direct effect whatsoever on the ultimate food products and leaves absolutely no undesirable reside in the animal or in the ultimate food products. In addition, since the deleterious organisms are prevented from multiplying, they, over time (for example, the 120-day finishing period in the feedlot), disappear through natural degradation from the feedlot environment, helping to eliminate that significant potential source of recontamination. The inhibitor product itself can be classified as a natural material of animal origin and as such can be used in almost any kind of feeding program. As the active ingredients are completely natural, they will work well with most feeds and feed additives, including molasses-based supplements.

All mammals and birds provide similar types of protection, which allow for an immediate immune response in their very young offspring until they too acquire the ability to make the antibodies for themselves. More specifically called passive antibody protection, this defense mechanism is passed to the young of mammals through the placenta, the mother's milk, or through both. The young of birds, however, receive their passive antibody protection through the store of antibodies in the eggs in which they develop from the embryonic stage. Birds, in particular, have the ability to "load up" their eggs as they are formed with a very large supply of antibodies concentrated many fold over which is present in the serum of the mother. In addition, avian antibodies are much more stable and resistant to inactivation through digestion than mammalian antibodies, especially under adverse conditions (Sterling, U.S. Pat. No. 5,753,268). Once immunized, the hen layers the unique IgY types immunoglobulins in the yolk while depositing the common chicken IgM and IgA immunoglobulins in the albumin (Leslie, 1969, Losch, 1986). The albumin helps give the heat resistance to the whole egg preparations and helps protect the avian antibodies. Furthermore, the large quantities of antibodies, which are placed in eggs, are much more exclusively those specific for the antigens to which the mother has most recently been exposed to and challenged by. This all results in the eggs of birds being the most ideal source for large quantities of economically produced, highly specific and stable antibodies. While the invention is illustrated by the use of chickens to produce avian antibody, other fowl including turkeys, ducks, geese, etc. may be used.

Specifically, groups are obtained of young hen chickens (typically Rhode Island Red, White Leghorns, hybrid crosses, or other breeds suited to large egg size or greater and to high volume egg production) which are about to reach egg laying age, about 16 weeks for chickens, on a schedule predetermined by the amount and timing of final product desired resulting in a steady continuous production stream. After a suitable period of isolation and acclimatization of about 2 to 4 weeks, each group will enter into an inoculation program using proprietary preparation of specific antigens to which an antibody is desired. The antigens may be obtained from commercial sources such as the American Type Culture Collection (ATCC). The antigen may be injected intramuscularly, but preferably injected sub-cutaneously. In approximately four weeks, the average egg collected will contain copious amounts of the desired specific antibody in a readily usable and stable form. The chickens may be reinoculated with the targeted antigen throughout the egg laying period to maintain the high antibody level.

Batches of eggs from predetermined groups of chickens are cracked, the contents are separated from the shells and mixed and preferably pasteurized (to eliminate potential pathogenic microorganism from the chicken and thus reduce potential contamination of feed). The pasteurized egg mixture can be used directly with standard feed rations. In addition, the total egg content may be dried using standard commercial methods, such as spray drying using ambient or hot air up to 50° C. and tested to determine overall titer or antibody level. The egg contents may be dried alone or on feed extenders such as dry soy or rice husks or the like. Standard test procedures are used, such as ELISA, or agglutination, or the like. The typical batch is then blended with batches from other groups of chickens at other average production levels resulting in a production lot with a standardized active ingredient level. The dried egg antibody microbial inhibitor material may be stored and shipped on carrier materials such as soybean hulls, boluses, and/or tablets. Dependent on the needs and specifications of the feed formulator and the final customer, the final antibody product may include some type of innocuous additive, such as dried whey or dried soy protein powder, dried soy or rice husks, or the like for formulate with feed ration. One egg produced and processed by the above procedures will yield a product sufficiently active and stable to provide at least as many as 350 to 700 daily doses of managed protection against microbial colonization. This method provides for the first time, an economical, safe, and effective means for controlling feed efficiency organisms in cattle and dairy herds, and an economical, safe and effective means for controlling *S. bovis* and *F. necrophorum* and other illness-causing or efficiency reducing organisms in cattle herds.

The present invention specifically addresses feed efficiency as it relates to beef cattle, and by extension dairy cattle and dairy herds, and to the problem of eliminating illness-causing organisms from cattle. However, the concept of preventing microbial adherence has great economic potential for a number of diverse food safety and production applications. One such field of application is in feed and water targeting specific undesirable microorganisms. An example of this application would include products to actively inhibit pathogenic or even spoilage microorganisms in animal feed formulated for chickens and other poultry. Another such field of application is as rinse aid ingredients targeted to specific undesirable microorganisms. Examples of this application include products to actively dislodge pathogenic or even spoilage microorganisms for use in solutions for spot cleaning and rinsing beef carcasses or for chilling poultry after they have been dressed.

The most successfully colonizing microorganisms, bacteria, viruses, and parasites, etc., have evolved a number of different types of molecules, referred to as "adherins," on their surfaces which can very tightly stick to one or more molecules that are part of the host's various surfaces. The adhesion inhibitor is an avian antibody of extraordinarily high specific activity which can very tightly bind to coat, cover, and obliterate these "adherins" which attach themselves to their hosts with a lock and key type of fit to very unique chemical structures. In addition to this direct attack, components of the complement system included in most biological fluids, such as blood, lymph, saliva, tears, and to some extent, intestinal secretions, recognize an antibody attachment as triggers for their many types of defensive activities. Specific antibody attachment and coating combined with the very likely mobilization of many other cellular defense systems, therefore quickly culminates inactivation and ultimately the destruction of the targeted microorganism.

The invention is further illustrated by the following examples:

EXAMPLE 1

Selection of Egg Laying Avian Hens

The strain of egg laying hens may vary with needs and uses. Any egg laying fowl hens may be immunized including chickens, turkeys, ducks, emus, or any other fowl. The common strains of egg laying chickens are the preferred and are usually selected for the number of eggs laid per year, size of egg, and ease of housing. Rhode Island Red, White Leghorn, and Red Sex Linked hybrids are the animals of choice based on egg size (large to ex-large, 50-65 gm) and were used for the immunization schedules. The ease of handling the animals and the size and uniformity of the eggs along with the number of eggs laid per hen per year were observed. Although any avian egg-laying hen could be used, for cost and ease of use, these chickens proved to work the best. The Red Sex Linked hybrid gave the most uniformity and greater number of eggs per animal. These animals produce a large to extra-large grade of eggs (50-65 gm) and up to 300 eggs a year per hen.

EXAMPLE 2

Preparation of Stock Culture

The American Type Culture Collection *Streptococcus bovis* (SB) Stock ATCC 15351 was used as the first model bacterium. The organism was isolated from Bovine rumen and can colonize in cattle. The ATCC Method for rehydration of the stock was followed. The bacterium is rehydrated in 10 ml of TSB Broth (Tryptase Soy Broth, Becton Dickinson), transferred to 5 ml of TSB sterile broth, and incubated overnight (approx. 18 hrs) at 37° C. Nice turbid growth was observed. This is used as stock as needed. It was streaked on Brain Heart Infusion Agar (Difco) for verification of colony production.

EXAMPLE 3

Preparation of Stock Culture

The American Type Culture Collection *Fusobacterium necrophorum* (FN) Stock ATCC 27852 was used as the second model bacterium. The organism was isolated from Bovine rumen and can colonize in cattle. The ATCC Method for rehydration of the stock was followed. The bacterium is rehydrated under anaerobic conditions and aseptically transferred to broth tube of TSB. Pre-reduced blood plates are inoculated with cell suspensor. Blood plates are incubated under anaerobic conditions of 37° C. Within 24-48 hours, agar surfaces which are circular or slightly irregular, grayish white and rough surface. The stock is made by aseptically transferring samples to Modified Chopped Meat Medium (#1490 Broth) grown under anaerobic conditions at 37° C.

EXAMPLE 4

Preparation of SB Antigen for "SB" Immunogen

The Brain Heart Infusion (BHI) is used for "SB" Antigen Production. It is a standard medium for stimulating adherence antigens for *Streptococcus Bovis*. These cultures must be grown under aerobic conditions. The stock culture is grown according to ATCC direction. Subcultures are grown in small amounts. Thioglycollate Media (Difco) is inoculated with the stock and incubated for 48 hours. Flask (Brain Heart Infusion Broth) are inoculated with subculture of *S. Bovis*. Flasks are incubated at 35° C. for 48-72 hours depending on apparent growth. Flasks are combined and the product is harvested using centrifugation at approximately 2500 rpm for 30 minutes, collected in tubes, and run at low speed for 30 minutes. Density is checked. The mixture is heated at 60° C. for 40 minutes (as needed) to inactivate. In some cases, 0.8% formaldehyde is added to make Stock immunogen. Mixture is centrifuged to remove whole cells. Dry weight is determined (approximately 20.5 mg/ml). The product is diluted with PBS, pH 7.4, 1 mg/ml for "SB" Immunogen.

EXAMPLE 5

Preparation of FN Antigens for "FN" Immunogen

The Modified Chopped Meat Medium is used for "FN" Antigen production. It is the standard medium for stimulation adherence antigens for *Fusobacterium necrophorum*. The stock culture is grown according to ATCC direction. Subcultures are grown in small amounts. Thiglycollate Media (Difco) is inoculated with the stock and incubated for 48 hours. Flask (Modified Chopped Meat Medium) are inoculated with subculture of *F. necrophorum*. Flasks are incubated at 37° C. for 48-72 hours depending on apparent growth. Flasks are combined and the product is harvested using centrifugation at approximately 2500 rpm for 30 minutes, collected in tubes, and run at low speed for 30 minutes. Density is checked. The mixture is heated at 60° C. for 40 minutes (as needed) to inactivate. In some cases, 0.8% formaldehyde is added to make stock immunogen. Mixture is centrifuged to remove whole cells. Dry weight is determined (approximately 20.5 mg/ml). The product is diluted with PBS, pH 7.4 mg/ml for "FN" immunogen.

Culturing was done in an isolation hood with a conventional incubator. Sterility was tested by inoculating thioglycollate tubes with each immunogen prep and incubating at 37° C. for 2-7 days.

EXAMPLE 6

Preparation of ELISA Plates Using SB Antigens for Monitoring Antibodies in Eggs, Chickens, and Feed "SB" ELISA's ninety-six well assay plates (flat bottom Costar) are coated using 100 μl/well with various concentrations of antigens (SB) combination: 10 mg-100 μg/ml in carbonate buffer, pH 9.6. Plates were incubated between 22-37° C. for up to 18 hours. The wells were aspirated to prevent cross-contamination. The plates were blocked with 380 μl/well of 0.05% BSA and incubated at 37.degree. C. for 1 hour. Plates were coated using alternative rows of positive or negative for controls. Plates were rinsed 1× with washer buffer containing Tween™ 20.

To run a test: One hundred microliters per well of diluted sample are added to wells in duplicate wells, and incubated at 37° C. for one hour. Goat anti-chicken IgG conjugate with Horseradish peroxidase (Kirkegard and Perry Laboratories; 1:1000-1:3000) was added. After 1-hour incubation, the substrate (TMB, KPL) was added according to manufacturer's instructions and the reaction is stopped after 10 minutes with 0.1 M phosphoric acid. Optical densities of the wells are determined in Dynatech ELISA Reader at 450 nm and the information was recorded for further data analysis.

EXAMPLE 7

Preparation of ELISA Plates Using FN Antigens for Monitoring Antibodies in Eggs, Chickens, and Feed "FN" ELISA's ninety-six well assay plates (flat bottom Costar) were coated using 100 μl/well with various concentrations of antigens (FN) combination: 10 mg-100 μg/ml in carbonate buffer, pH 9.6. Plates were incubated between 22-37° C. for up to 18 hours. The wells were aspirated to prevent cross-contamination. The plates were blocked with 380 μl/well of 0.05% BSA and incubated at 37° C. for 1 hour. Plates were coated using alternative rows of positive or negative for controls. Plates were rinsed 1× with washer buffer containing Tween™ 20.

To run a test: One hundred microliters per well of diluted sample were added to wells in duplicate wells, and incubated at 37° C. for one hour. Goat anti-chicken IgG conjugate with Horseradish peroxidase (Kirkegard and Perry Laboratories; 1:1000-1:3000) was added. After 1-hour incubation, the substrate (TMB, KPL) was added according to manufacturer's instructions and the reaction is stopped after 10 minutes with 0.1 M phosphoric acid. Optical densities of the wells are determined in Dynatech ELISA Reader at 450 nm and the information is recorded for further data analysis.

EXAMPLE 8

Immunization of Chicken with SB Immunogen

Selected egg laying hens (White Leghorn Hy-Line W98), approximately 16-19 weeks old, are injected with the stock "SB" Immunogen. Four injections (500 μg, 100 μg, 250 μg, and 500 μg) are given 1 week apart. Serum samples are collected two weeks after the last initial injection. If boosters are needed, 100 μg is given in each booster (every 6 months). Within 4 weeks, hens produced excellent antibodies in the eggs.

EXAMPLE 9

Immunization of Chicken with FN Immunogen

Selected egg laying hens (White Leghorn Hy-Line W98), approximately 16-19 weeks old, are injected with the stock "FN" Immunogen. Four injections (500 μg, 100 μg, 250 μg, and 500 μg) are given 1 week apart. Serum samples are collected two weeks after the last initial injection. If boosters are needed, 100 μg is given in each booster (every 6 months). Within 4 weeks, hens produced excellent antibodies in the eggs.

EXAMPLE 10

Process for Preparation of Whole Egg material

Specific commercial strains of Hy-Line W98 egg laying hens are immunized with specific immunogen. Eggs are collected from hens on a daily basis. They are washed with soap and water, and then dripped in 0.05% bleach. The shells are air-dried.

EXAMPLE 11

Analysis of Production Eggs Over Time: "SB" Immunogen

During the product development phase, samples of the whole egg preparations were analyzed using the ELISA systems for "SB" Immunogen to monitor activity over time after the initial immunization schedule was completed. Selected animals from each group were placed into the production group. The average ELISA OD readings for the fourth through the sixth months are given in the table below. The eggs were sampled using 250 μ of the whole egg and diluted 1:500 and 1:2,500 in PBS buffer and then run in the appropriate ELISA to determine the average OD reading at each dilution. The negative control readings are subtracted from each reading. The injected immunogens stimulated different responses in the animals along with good specificity.

EXAMPLE 12

Preparation of Stock Production Whole Egg Reagents

Random groups of selected eggs are combined from the two Immunogen groups, to be used to produce production batches of whole egg reagents. The eggs are randomized and shell removed. The whole egg is mixed well and pasteurized using standard conditions (60° C. {140° F.}) for 3.5 min. (Charley, H. and C. Weaver, 3$^{rd}$ edition, Food: a scientific approach, Merrill-Prentice Hall, P. 350, 1998). Temperature is recorded with a Fisher traceable scientific thermometer. Once pasteurized, samples are tested for activity and stored at 4° C. in the liquid format or stored until dried or sprayed onto carriers. Samples of 250 µl were analyzed. Examples of results for ELISAs are given. Negative controls are subtracted to get final OD reading.

Pasteurized Whole Egg: *S. Bovis*

| Sample | *Streptococcus bovis* |
| --- | --- |
| Oct. 22, 2002 B9P2 | 0.342 OD S/N 4.490 |
| Oct. 22, 2002 B9P2 | 0.348 OD S/N 4.663 |
| Sep. 4, 2002 B4P1 | 0.220 OD S/N 1.189 |
| Sep. 4, 2002 B4P1 | 0.253 OD S/N 3.074 |
| Aug. 7, 2002 B3P2 | 0.407 OD S/N 2.825 |
| Aug. 7, 2002 B3P2 | 0.428 OD S/N 3.048 |
| Jul. 15, 2002 B4P2 | 0.559 OD S/N 5.819 |
| Jul. 15, 2002 B4P2 | 0.654 OD S/N 10.909 |

Pasteurized Whole Egg: *F. necrophorum*

| Sample Liquid: | *Fusobacterium necrophorum* |
| --- | --- |
| 120402BL-1P1b | 0.281 OD S/N 2.82 |
| 120402BL-1P1b | 0.188 OD S/N 2.65 |
| 01093BL-1P1a | 0.180 OD S/N 2.27 |
| 01093BL1P1a | 0.152 OD S/N 2.08 |
| 010903BL-2P1 | 0.157 OD S/N 2.8 |
| 010903BL-2P1 | 0.153 OD S/N 2.55 |

EXAMPLE 13

Production of Liquid Egg Product

The liquid, whole eggs can be dispensed in water or placed directly on to feed ration and mixed well. A preferred method is as follows: eggs are collected and prepared as given in Example #10 and #12. The specific whole egg material is collected and mixed with food grade molasses (Dark Molasses, Best Brands, Inc, St. Paul, Minn. or Molasses: Food Grade, Evolution Habitats, New Roads, La.), PBS, pH 7.4, Stabilizers (1% Vitamin E dispensable liquid, αL alpha tocopherl acetate, 400 iu/gram from I.D. Russell Company Labs, Longmont, Colo.) or pure food grade soybean oil, 0.1% Vanilla (Preferred Products, Inc. Eden Prairie, Minn.), 0.1% Food grade preservative (70% Potassium Sorbate, 27% Citric Acid, 3.0% Sodium Benzoate, Ashland-Fine Ingredients Division, Columbus, Ohio, Food grade). The materials are mixed well and then pasteurized at 140° F. for 3.5 minutes in a food pasteurizer, (Model p. 3000 the Schlueter Company, Janesville, Wis.; following SOP). The product can be sprayed directly onto standard rations as long as it is mixed well.

The preferred level is 1.5-2.5 ml of feed additive per animal per day. This can be given directly to the animal in the daily feed ration or mixed with the water supply. The following are examples of ingredients for the antibody in liquid format: Specific prepared whole egg, PBS, pH 7.4, molasses, stabilizers (1% vitamin E or soy oil, 0.1% vanilla, 0.1% food grade preservatives).

Batches of product were manufactured and sampled. The samples were sent to Minnesota Valley Testing Services. The following averages were determined:

| Moisture | Fat | Fiber | Protein |
| --- | --- | --- | --- |
| 65.50% | 5.5% | 0.28% | 7.70% |

EXAMPLE 14

Coating of Feed Additive Carriers

Although liquid whole eggs can be dispensed in water or feed supplies, or in a dried format as whole egg, use of a carrier helps distribute the material in a uniform method. This makes it easier for mixing with standard feeds. A number of carriers can be used to provide a vehicle as a feed additive as needed. Soy hulls in crude, refined and pelted format, rice hulls, corn, cottonseed hulls, distilled dried grains, beet pulp or any other similar carriers. The preferred carrier for cattle is a pelleted soybean hull. The preferred method is as follows: The specific whole egg material is collected and mixed with food grade molasses (Dark Molasses, Best Brands, Inc, St. Paul, Minn. or Molasses: Food Grade, Evolution Habitats, New Roads, La.), PBS, pH 7.4, Stabilizers (1% Vitamin E dispensable liquid, αL alpha tocopherl acetate, 400 iu/gram from I.D. Russell Company Labs, Longmont, Colo.) or pure food grade soybean oil, 0.1% Vanilla (Preferred Products, Inc. Eden Prairie, Minn.), 0.1% Food grade preservative (70% Potassium Sorbate, 27% Citric Acid, 3.0% Sodium Benzoate, Ashland-Fine Ingredients Division, Columbus, Ohio, Food grade). The materials are mixed well and then pasteurized at 140° F. for 3.6 minutes in a food pasteurizer, (Model p. 3000 the Schlueter Company, Janesville, Wis.; following SOP). The product can be sprayed directly onto standard rations as long as it is mixed well.

The production pasteurized whole egg prep is coated on to the carrier and either given directly to the animals or dried to 10-14% moisture. Approximately 900 ml of whole, pasteurized egg mixture is then enrobed onto soybean hull pellets (501 lbs)(harvest States, Mankato, Minn.). The pellets are enrobed and augered to dry (10-14%) at room temperature (70-80 ° F.). The pellets are either bagged or used in bulk. The feed additive is mixed with the standard animal feed. The preferred level is 10-15 lbs of feed additive to 2000 lbs of animal feed.

The following are examples of ingredients for the antibody coated format: soybean hull pellets, specific prepared whole egg, PBS, pH 7.4, molasses, stabilizers (1% vitamin E or soy oil, 0. 1% vanilla, 0. 1% food grade preservatives).

Ten batches of product were manufactured and sampled. The samples were sent to Minnesota Valley Testing Services. The following averages were determined:

| Moisture | Ash | Fat | Fiber | Protein |
| --- | --- | --- | --- | --- |
| 11.11% | 4.55% | 3.34% | 30.68% | 12.7% |

EXAMPLE 15

Analysis of Feed Additives for Antibody Activity: "SB" Product

"SB" product contains antibodies against *S. bovis*. Samples of the coated hulls were analyzed using the ELISA systems for "SB" Immunogens to monitor activity after pasteurizing, spraying, drying, and storage. Good antibody response was recorded after the processing of the Production Whole Egg batches and drying on crude soybean hulls. One-gram samples of the 15 lbs of coated hulls were extracted and analyzed. Data for three batches taken 3-5 months apart is given in the table below (Average OD-Negative Control and Signal to Noise ratio (S/N)):

| Batch: Coated Hulls | SB Immunogen |
|---|---|
| Batch #1 1:30 | 0.345OD S/N 4.58 |
| Batch #2 1:30 | 0.237OD S/N 2.63 |
| Batch #3 1:30 | 0.418OD S/N 2.94 |
| Batch #4 1:30 | 0.607OD S/N 8.36 |

EXAMPLE 16

Analysis of Feed Additives for Antibody Activity: "FN" Product

"FN" product contains antibodies to *F. necrophorum*. Samples of the coated hulls were analyzed using the ELISA systems for "FN" Immunogens to monitor activity after pasteurizing, spraying, drying, and storage. Good antibody response was recorded after the processing of the Production Whole Egg batches and drying on crude soybean hulls. One-gram samples of the 15 lbs of coated hulls were extracted and analyzed. Data for three batches is given in the table below (Average OD-Negative Control and Signal to Noise ratio (S/N)):

| Feed: | FN Immunogen |
|---|---|
| 011003BL | 0.140 OD S/N 1.87 |
| 011003BL | 0.015 OD S/N 1.08 |
| 012103BL 1× | 0.120 OD S/N 1.86 |
| 012103BL 1× | 0.158 OD S/N 1.99 |
| 012103BL 2× | 0.149 OD S/N 1.7 |
| 012103BL 2× | 0.131 OD S/N 1.64 |
| 012103BL 3× | 0.150 OD S/N 1.75 |
| 012103BL 3× | 0.198 OD S/N 1.91 |

EXAMPLE 17

Animal Testing #1

Seventeen rumen cannulated beef steers (1000 lbs.) were paired by weight and allocated to one of four dietary treatments. Dietary treatments consisted of delivering increasing doses (1×, 2×, 3×) of polyclonal antibody preparation against *S. bovis* in a soy hull-based carrier pellet (9 steers) or the soy-hull-based carrier pellet (8 steers) for 28 days. Half of the steers were fed a protein, vitamin and mineral supplement containing Rumensin and Tylan, and the other half did not receive Rumensin or Tylan in the supplement. The Rumensin/Tylan treated steers were divided equally between the test and control groups.

Diets were formulated to contain 0.64 Mcal $Ne_g$/lb. DM, 12.5% CP, 0.65% Ca and 0.35% P. Diets were mixed in a total-mixed-ration feeding cart and delivered once daily. Dietary treatments were given as top-dressed once daily. Refusals were limited by feeding diets to 97% of ad libitum. Dry matter ("DM") intake was measured daily. Water was accessible at all times.

For Experiment #1, data was collected over the time period corresponding to the baseline (day 0) and day 14. Steers that received antibody treatment had counts of *S. bovis* that were lower (P=0.02) than in steers that received no antibody treatment. Also, when comparing *S. bovis* counts on day 14 vs. day 0, steers treated with antibody had decreasing counts, while those that were not treated had increasing counts. This is shown in FIG. 1 and Table 1.

TABLE 1

*S. bovis* counts collected in rumen fluid on day 0 and day 14 of a 14-day feeding program where rumen cannulated steers were treated (antibody against *S. bovis* at single, double or triple dose) or not.

| Item | Un-treated | Single | Double | Triple | Treated |
|---|---|---|---|---|---|
| *S. bovis*, day 0 | $8.3 \times 10^8$ | | | | $6.3 \times 10^8$ |
| *S. bovis*, day 14 | $1.1 \times 10^9$ | | | | $9.7 \times 10^7$ |
| *S. bovis* #'s[2] | $9.8 \times 10^8$ | $2.6 \times 10^8$ | $3.5 \times 10^8$ | $4.6 \times 10^8$ | |

[2] Average counts from samples collected on days 0 and 14 presented according to each dose.

TABLE 2

Dose Response of Antibody from 8 to 28 days on Feed

| | Dose | | | | |
|---|---|---|---|---|---|
| Item | 0 | 1 | 2 | 3 | P-Value |
| *S. bovis* | 5.88E8 | 1.17E8 | 2.29E8 | 1.47E8 | 1.0192 |
| Effect, % | — | 80.1 | — | 75.0 | |
| pH @ d 14 | 6.39 | 6.59 | 6.39 | 6.44 | 0.8588 |
| AB vs none | | 0 | | 1 | |
| *S. bovis* | | 5.89E8 | | 1.48E8 | 0.0107 |
| Effect, % | | — | | 75.0 | |

For Experiment #2, a dose response (Table 2) was recorded over a 20 day period where there is a significant drop in isolated S. bovis in the Test animals versus the Controls. The data indicates a drop in S. bovis (80.1% and 75.0%) over a 20 day period for treated animals. Although there is a clear drop in numbers for 1×, 2× or 3× material, no significant change was observed with 2× or 3× delivery when compared to 1×. This may be due to blocking antibodies in concentrated preparation.

TABLE 3

F. necrophorum counts collected in rumen fluid on day 1 and day 12 of a 12-day feeding program where rumen cannulated steers were treated (antibody against F. necrophorum at single dose) Versus Control (No Antibody)

| F. necrophorum Average, Test, Day 0 | F. necrophorum Average, Test, Day 12[a] |
|---|---|
| 4.79E+04/ml Rumen Fluid | 1.51E+04/ml Rumen Fluid |
| Control, F. necrophorum Average, Day 0 | Control, F. necrophorum Average, Day 12[a] |
| 5.08E+04/ml Rumen Fluid | 2.09E+05/ml Rumen Fluid |

[a]Within variable means, the difference between control and test are statistically significant different at $P = <0.024$.

In Experiment #3, the data collected and given in Table 3 from this experiment shows significant reduction ($P<0.05$) of F. necrophorum in animals fed antibodies as an additive to standard ration.

TABLE 4

Response to S. bovis Antibody at 70 and 91 days on Feed

| | Hours - Post Feeding | | | | |
|---|---|---|---|---|---|
| Item | 0 | Control 5.5 | 0 | Test 5.5 | P-Value |
| S. bovis | 1.82E8 | 3.89E8 | 7.08E7 | 6.92E7 | 0.0467 |
| Effect, % | | 74.0 | | | |
| pH | 5.91 | 5.42 | 6.54 | 5.61 | 0.0219 |
| 10 d Post Treatment | 1.29E8 | | 8.91E7 | | 0.6077 |
| Effect, % | | | | 30.8 | |

In summary, these studies have resulted in preparations of antibodies against S. bovis and F. necrophorum that do reduce target bacterial populations. The effect on S. bovis populations decreases over days on feed. This is due to an inherent decrease in S. bovis. As shown in Table 4, however, there are responses to the antibodies between days 70 and 90 on feed. At 90 Days on feed, counts of S. bovis were 75% lower for Test cattle. At 90 Days on feed, ruminal pH of Test cattle was 7% greater. After 10 days post-treatment, effect of S. bovis antibodies on counts of S. bovis disappeared.

EXAMPLE 18

Animal Testing #2

Two hundred twenty eight Angus crossbred steer calves (550 lb) were assigned to one of sixteen pens within weight class. Pens were randomly assigned to one of four dietary treatments. Dietary treatments were isocaloric, isonitrogenous diets based on corn grain (50:50 high moisture corn: dry rolled corn) and corn silage. Dietary treatments consisted of delivering a dose of polyclonal antibody preparation against S. bovis or F. necrophorum or both in a soy hull-based carrier pellet (4 pens) or the soy-hull-based carrier pellet (4 pens) for the duration of the feeding period. A total of 240 g of soy-hulls were offered/head daily. However, depending on treatment schedule, some pens received only 240 g soy-hulls/head (control), soy-hulls (120 g/head), and a polyclonal preparation infused in soy-hulls (120 g/head, F necrophorum or S. bovis), and a polyclonal preparation infused in soy-hulls (120 g/head F necrophorum and 120 g/head S. bovis). A supplement was formulated to meet protein, vitamin, and mineral requirements. Protein and energy content of these diets estimated from book values are 12.5% and 0.62 Mcal $Ne_g$/lb. (dry basis). Dietary treatments were top-dressed once daily.

Steers were dewormed, vaccinated against viral and bacterial diseases (IBR, BVD, $PI_3$, BRSV, 7-way Clostridium sp., and haemophilus somnus), and adapted for a 4-week period. Steers were housed in a confinement barn bedded with straw at least once weekly; bedding was allowed to accumulate for the duration of the feeding period. Feed apron was scraped twice weekly. Feed ingredients were added and mixed to a truck-mounted mixer. Feed offerings (once daily) were made according to a bunk call that considers the preceding 3-day running feed delivery and bunk scores to achieve ad libitum feeding. Feed offerings and refusals were measured on monthly composites of samples collected weekly.

Steers were implanted with a TBA-based implant initially, and according to projected slaughter date (within 85 to 100 days before slaughter). Steers were sent to market when 65% of the steers in the pen reached choice grade as assessed visually.

An initial shrunk weight was taken in the morning after withholding feed and water for 16 hours. Interim weights were taken every 28 days before feeding. Final weight was calculated from hot carcass weight using a common dressing percentage of 62.5. Steers were processed at a commercial abattoir (IBP, Dakota City, Nebr.) by standard, USDA-approved procedures. Rib eye, proportion of kidney, pelvic and heart fat depot (KPH %), and fat depth were measured by university personnel. USDA inspectors assigned to the plant measure quality and yield grade.

Data on weight, gain, DM intake, DM required/100 lb gain, and carcass characteristics was analyzed for effects of diet using the pens as the experimental unit in ANOVA for a randomized block design with a factorial arrangement of treatments. Treatments:

1) Control (8 oz. Soybean hull carrier per head per day)
2) 4 oz. $SB^a$ product+4 oz. Soybean hull carrier per head per day
3) 4 oz. $FN^b$ product+4 oz. Soybean hull carrier per head per day
4) 4 oz. $FN^b$ product+4 oz. $SB^a$ product per head per day
   [a]SB Product: The S. bovis antibodies in liquid or dried on coated pellets.
   [b]FN Product: The F. necrophorum antibodies in liquid or dried on coated pellets.

TABLE 5

Feedlot performance of steers fed antibodies 56 days against S. bovis, F. necrophorum, or both.

| | Treatment | | | | |
|---|---|---|---|---|---|
| Item | Control | SB | FN | SB & FN | P-value |
| Start wt., il | 598 | 600 | 603 | 603 | 0.624 |
| 56 d wt | 860 | 873 | 876 | 864 | 0.162 |
| Total gain* | 237 | 247 | 247 | 236 | 0.078 |
| ADG* | 4.23 | 4.40 | 4.41 | 4.21 | 0.084 |
| Total DMI | 1069 | 1077 | 1083 | 1067 | 0.899 |

TABLE 5-continued

Feedlot performance of steers fed antibodies 56
days against *S. bovis*, *F. necrophorum*, or both.

| | Treatment | | | | |
|---|---|---|---|---|---|
| Item | Control | SB | FN | SB & FN | P-value |
| Daily DMI | 19.09 | 19.23 | 19.33 | 1905. | 0.897 |
| FTG | 4.53 | 4.37 | 4.38 | 4.53 | 0.238 |

*Total Gain and ADG figures reflect a 3% liveweight shrink

TABLE 7

Feedlot performance of steers fed antibodies 140
days against *S. bovis*, *F. necrophorum*, or both

| | Treatment | | | |
|---|---|---|---|---|
| Item | Control | SB | FN | SB & FN |
| No. of pens | 4 | 4 | 4 | 4 |
| Start wt, lb | 598 | 601 | 603 | 603 |
| 140 d wt, lb | $1199^x$ | $1221^y$ | $1228^y$ | $1215^y$ |
| ADG, lb | $4.03^x$ | $4.17^y$ | $4.20^y$ | $4.13^y$ |
| Total gain, lb | $601^x$ | $620^y$ | $625^y$ | $612^y$ |
| Dry matter intake, lb/d | 20.50 | 20.58 | 20.90 | 20.52 |
| DM required/lb gain, lb | 5.08 | 4.94 | 4.98 | 4.97 |

$x,y$ Means within a row lacking common superscripts differ P < 0.05.

TABLE 6

Feedlot performance of steers fed antibodies 84
days against *S. bovis*, *F. necrophorum*, or both

| | Treatment | | | |
|---|---|---|---|---|
| Item | Control | SB | FN | SB & FN |
| No. of Pens | 4 | 4 | 4 | 4 |
| Start wt. lb | 598 | 601 | 603 | 603 |
| 84 d wt, lb | $965^x$ | $983^y$ | $984^y$ | $974^{xy}$ |
| ADG, lb* | $4.02^x$ | $4.20^y$ | $4.19^y$ | $4.08^{xy}$ |
| Total gain, lb* | $338^x$ | $352^y$ | $351^y$ | $342^{xy}$ |
| Dry matter intake, lb/d | 19.24 | 19.23 | 19.65 | 19.21 |
| Total intake, lb | 1616 | 1615 | 1650 | 1613 |
| DM required/lb gain, lb | 4.79 | 4.59 | 4.70 | 4.71 |

$x,y$ Means within a row lacking common superscripts differ P < 0.05
*Total Gain and ADG figures reflect a 3% liveweight shrink.

The 140 day Body Weight, Average Daily Gain and Total Gain were all significantly better in the test cattle when compared to the controls. The DM required/pound of gain was numerically less for the test cattle compared to the controls, but P>0.05. Expectations are 25-30% liver abscesses in a typical group of cattle fed at this feedlot. Only 15% liver abscesses were found in total, meaning a likely decrease in acidosis, rumen abscesses and *F. necrophorum* in the test cattle.

EXAMPLE 19

Animal Testing #3

In order to study the effect of *S. bovis* antibodies coated onto soy hull pellets, a series of animals were randomly gate selected and placed into different pens. There were 6 pens for controls and 6 pens each for each separate treatment. Treatment 1—*S. bovis* antibody coated pellets for 35 days. Treatment 2—*S. bovis* antibody coated pellets for the entire feeding period. The number of animals in each pen was as follows:

| | Control | Treat 1 | Treat 2 |
|---|---|---|---|
| Rep 1 | 233 | 233 | 233 |
| Rep 2 | 218 | 219 | 219 |
| Rep 3 | 264 | 266 | 266 |
| Rep 4 | 241 | 240 | 238 |
| Rep 5 | 215 | 210 | 210 |
| Rep 6 | 239 | 240 | 239 |

The animals were fed standard high-energy "hot" ration. The treatment additives were mixed with the standard ration. The feeding trial covered approximately 140 days.

Summary of Results for Animal Testing #3 are as follows:

| | | Pen # in pen | # of animals av. | Dm. total | Gain | ADG conv. | Dm. |
|---|---|---|---|---|---|---|---|
| Rep #1 | Full Term | 8241 | 233 | 22.30 | 373.43 | 2.79 | 8.00 |
| | 35 day | 8242 | 233 | 21.03 | 350.55 | 2.62. | 8.02 |
| | Control | 8243 | 233 | 21.04 | 350.51 | 2.62 | 8.02 |
| Rep #2 | Full Term | 8237 | 219 | 23.43 | 430.32 | 3.44 | 6.87 |
| | 35 day | 8238 | 219 | 22.99 | 432.69 | 3.48 | 6.61 |
| | Control | 8239 | 218 | 22.96 | 417.17 | 3.34 | 6.81 |
| Rep #3 | Full Term | 8234 | 266 | 22.92 | 508.89 | 3.15 | 7.37 |
| | 35 day | 8235 | 266 | 22.92 | 504.28 | 3.12 | 7.36 |
| | Control | 8236 | 264 | 22.56 | 494.72 | 3.06 | 7.29 |
| Rep #4 | Full Term | 8248 | 238 | 22.16 | 425.65 | 3.15 | 7.26 |
| | 35 day | 8247 | 240 | 22.11. | 427.89 | 3.17 | 7.25 |
| | Control | 8246 | 241 | 21.24 | 409.88 | 3.05 | 7.21 |
| Rep #5 | Full Term | 8255 | 210 | 19.32 | 382.05 | 2.91 | 6.73 |
| | 35 day | 8254 | 210 | 19.67 | 383.8 | 2.93 | 6.81 |
| | Control | 8253 | 215 | 19.78 | 361.64 | 2.76 | 7.26 |
| Rep #6 | Full Term | 8258 | 239 | 22.44 | 430.54 | 3.08 | 7.28 |
| | 35 day | 8259 | 240 | 21.48 | 426.98 | 3.04 | 7.05 |
| | Control | 8260 | 239 | 21.80 | 424.95 | 3.04 | 7.18 |

As summarized and recorded below, the resulting data shows a significantly higher gain, both as average and total gain, for cattle receiving the treatment for either 35 days or the complete test period. There does not appear to be significant advantage for full time treatment over 35 days. In addition, a larger standard profit can be realized from the treated cattle. The other variables in the table below were not significant.

Statistical Analysis for Animal Testing #3

| No. | Variable | Control | 35 Days | Full Time | Statistical Significance at $\alpha = .05$ | Least Significant Difference |
|---|---|---|---|---|---|---|
| 1 | Gain | 409.8$^A$ | 421.0$^B$ | 424.7$^B$ | Yes | 7.8 |
| 2 | ADG | 2.98$^A$ | 3.06$^B$ | 3.09$^B$ | Yes | 0.06 |
| 3 | Total Gain | 96,688$^A$ | 98,760$^B$ | 99,722$^B$ | Yes | 1,477 |
| 4 | Standard Profit | $14,995$^A$ | $16,324$^B$ | $16,207$^B$ | Yes | $1,150 |
| 5 | DM Conv. | 7.32 | 7.18 | 7.23 | No | 0.17 |
| 6 | Percent Choice | 56.3 | 60.8 | 55.7 | No | 6.3% |
| 7 | DM Consumption | 21.73 | 21.89 | 22.25 | No | 0.52 |
| 8 | 1s and 2s | 62.9 | 62.2 | 60.9 | No | 6.6% |
| 9 | Adjusted Dressing | 62.14 | 62.20 | 62.36 | No | 0.28% |
| 10 | COG | 61.19 | 60.10 | 60.27 | No | $1.25 |

$^{AB}$Within a variable means, the two treatments are not statistically significant different at $\alpha = .05$ using Fishers protected LSD.

Any microorganisms which colonize the alimentary tract of host animals must possess the capability of sticking or adhering to that surface in order to multiply. Organisms that promote the production of harmful accumulations of lactic acid in the rumen such as *Streptococcus bovis* and *Lactobacillus* spp. are no exception. The adherence inhibitors of this invention strongly interfere with the adherence and, on a cumulative basis, thereby prevent the specific targeted microorganism from colonizing and multiplying. Through the vehicle of a simple daily feed additive, the product essentially supplies the host with a specific antibody preparation designed not to cure any disease in the animal but to dislodge any resident bacteria and to prevent the attachment of any newly introduced bacteria in the alimentary tract. The adherence inhibitor has no direct effect on the host itself, leaves no undesirable residue in the animals and thus has no affect whatsoever on the ultimate food products.

It is apparent that many modifications and variations of this invention as hereinbefore set forth may be made without departing from the spirit and scope thereof. The specific embodiments described are given by way of example only and the invention is limited only by the terms of the claims.

The embodiments of the invention in which an exclusive property or privilege is claimed are defined as follows:

1. A method for reducing or eliminating the incidence of liver abscess in food animals caused by the presence of liver abscess forming bacteria in the animal by inhibiting the ability of the bacteria to adhere to the rumen of the animal to reduce the ability of the bacteria to multiply, said method comprising:
   a. inoculating female birds, in or about to reach their egg laying age, with *Fusobacterium necrophorum* whose colonization results in liver abscess forming bacteria and the *Fusobacterium necrophorum* having been cultured to stimulate adherence FN antigens;
   b. allowing a period of time sufficient to permit the production in the birds of antibody to *Fusobacterium necrophorum* adherence antigens;
   c. harvesting the eggs laid by the birds; and
   d. separating the antibody-containing contents of said eggs from the shells;
   e. drying said separated antibody-containing contents of said eggs;
   f. distributing the resulting dried egg antibody product substantially uniformly through an animal feed or water; and
   g. supplying the resulting antibody-containing animal feed or water to food animals to inhibit adherence of *Fusobacterium necrophorum* to the rumen thereby reducing or eliminating the incidence of liver abscess in food animals.

2. The method of claim 1 further comprising providing a dry feed carrier material, and drying the separated antibody-containing contents of said eggs by coating said dry carrier material with said separated antibody-containing contents of said eggs.

3. The method of claim 2 wherein:
   the dry feed carrier material comprising soybean hulls, rice hulls, corn, cottonseed hulls, distilled dried grains or beet pulp.

4. The method of claim 1 further comprising mixing the antibody-containing contents of said eggs with a liquid extender.

5. The method of claim 4 wherein:
   said liquid comprises liquid molasses or PBS.

* * * * *

UNITED STATES PATENT AND TRADEMARK OFFICE
CERTIFICATE OF CORRECTION

| | | |
|---|---|---|
| PATENT NO. | : 7,560,109 B2 | Page 1 of 1 |
| APPLICATION NO. | : 11/786525 | |
| DATED | : July 14, 2009 | |
| INVENTOR(S) | : Peter Nash et al. | |

It is certified that error appears in the above-identified patent and that said Letters Patent is hereby corrected as shown below:

Title page,
Item (52) please correct the title with --IMMUNOGEN ADHERENCE INHIBITOR DIRECTED TO ORGANISMS THAT CAUSE LIVER ABSCESSES IN RUMINANTS AND THE METHOD OF MAKING AND USING IT--

Col. 16, Table 5, after "Start wt.,", replace "il" with --lb.--.

Signed and Sealed this

Eleventh Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,560,109 B2  Page 1 of 1
APPLICATION NO. : 11/786525
DATED : July 14, 2009
INVENTOR(S) : Peter Nash et al.

It is certified that error appears in the above-identified patent and that said Letters Patent is hereby corrected as shown below:

Title page,
Item (54) please correct the title with --IMMUNOGEN ADHERENCE INHIBITOR DIRECTED TO ORGANISMS THAT CAUSE LIVER ABSCESSES IN RUMINANTS AND THE METHOD OF MAKING AND USING IT--

Col. 16, Table 5, after "Start wt.,", replace "il" with --lb.--.

This certificate supersedes the Certificate of Correction issued May 11, 2010.

Signed and Sealed this

Fifteenth Day of June, 2010

David J. Kappos
*Director of the United States Patent and Trademark Office*